United States Patent

Zarbatany et al.

[11] Patent Number: 5,810,867
[45] Date of Patent: Sep. 22, 1998

[54] DILATATION CATHETER WITH VARIED STIFFNESS

[75] Inventors: David J. Zarbatany, Encinitas; Rafael Pintor, San Diego, both of Calif.; Maurice T. Verbeek, Geleen, Netherlands

[73] Assignee: Medtronic, Inc., Minneapolis, Minn.

[21] Appl. No.: 847,897

[22] Filed: Apr. 28, 1997

[51] Int. Cl.[6] .................................................. A61M 29/00
[52] U.S. Cl. ............................ 606/191; 606/194; 604/96; 604/164
[58] Field of Search .................. 604/96, 164; 606/194, 606/191

[56] References Cited

U.S. PATENT DOCUMENTS

| | | | |
|---|---|---|---|
| 4,762,129 | 8/1988 | Bonzel | 606/194 |
| 5,040,548 | 8/1991 | Yock | 128/898 |
| 5,061,273 | 10/1991 | Yock | 606/194 |
| 5,129,887 | 7/1992 | Euteneuer et al. | 606/194 |
| 5,192,295 | 3/1993 | Danforth et al. | 604/96 |
| 5,382,234 | 1/1995 | Cornelius et al. | 604/96 |
| 5,395,334 | 3/1995 | Keith et al. | 604/102 |
| 5,409,458 | 4/1995 | Khairkhahan et al. | 604/96 |
| 5,425,711 | 6/1995 | Ressemann et al. | 604/96 |
| 5,451,233 | 9/1995 | Yock | 606/194 |
| 5,458,639 | 10/1995 | Tsukashima et al. | 604/97 |
| 5,480,383 | 1/1996 | Bagaoisan et al. | 604/96 |
| 5,484,409 | 1/1996 | Atkinson et al. | 604/96 |
| 5,496,346 | 3/1996 | Horzewski et al. | 606/194 |
| 5,527,298 | 6/1996 | Vance et al. | 606/191 |
| 5,545,138 | 8/1996 | Fugoso et al. | 604/102 |
| 5,549,552 | 8/1996 | Peters et al. | 604/96 |
| 5,549,553 | 8/1996 | Ressemann et al. | 604/96 |

FOREIGN PATENT DOCUMENTS 9217236  10/1992  WIPO .

*Primary Examiner*—Michael Powell Buiz
*Assistant Examiner*—Julian W. Woo
*Attorney, Agent, or Firm*—John R. Duncan; Dianne M. F. Plunkett; Harold R. Patton

[57] ABSTRACT

A dilation catheter having a balloon inflation shaft with an inflation lumen into which a stiffening wire extends and a guidewire shaft having a guide wire lumen adjacent to the balloon. The stiffening wire includes at least two stepped diameter reductions along its length to vary stiffness from a stiff proximal end providing improved pushability to a less stiff distal end providing improved trackability. A manifold at the inflation shaft proximal end includes a handle for adjusting the distance the stiffening wire extends into the inflation lumen to allow stiffness to be optimized. The handle includes a tubular flange frictionally engaging the manifold to prevent inadvertent handle movement. The balloon inflation shaft and guidewire shafts are bonded together in a manner producing an assembly having a circular cross section for improved connection to a circular balloon and improved catheter performance.

11 Claims, 5 Drawing Sheets

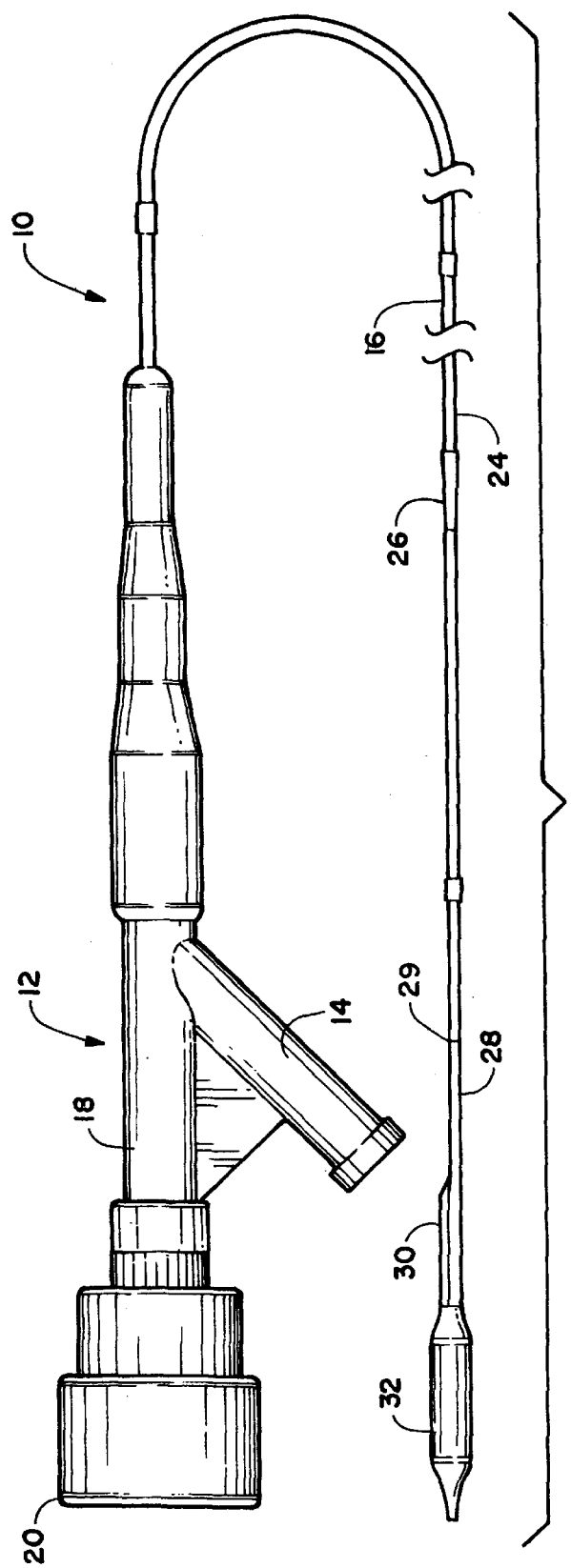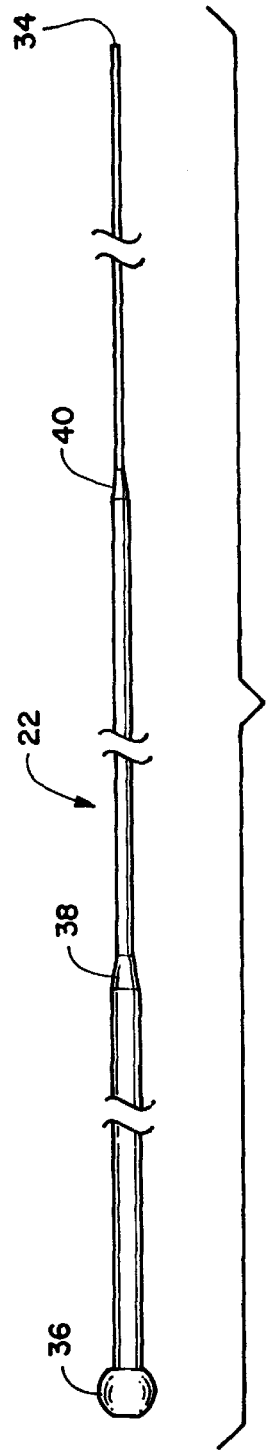
FIGURE 1
FIGURE 2

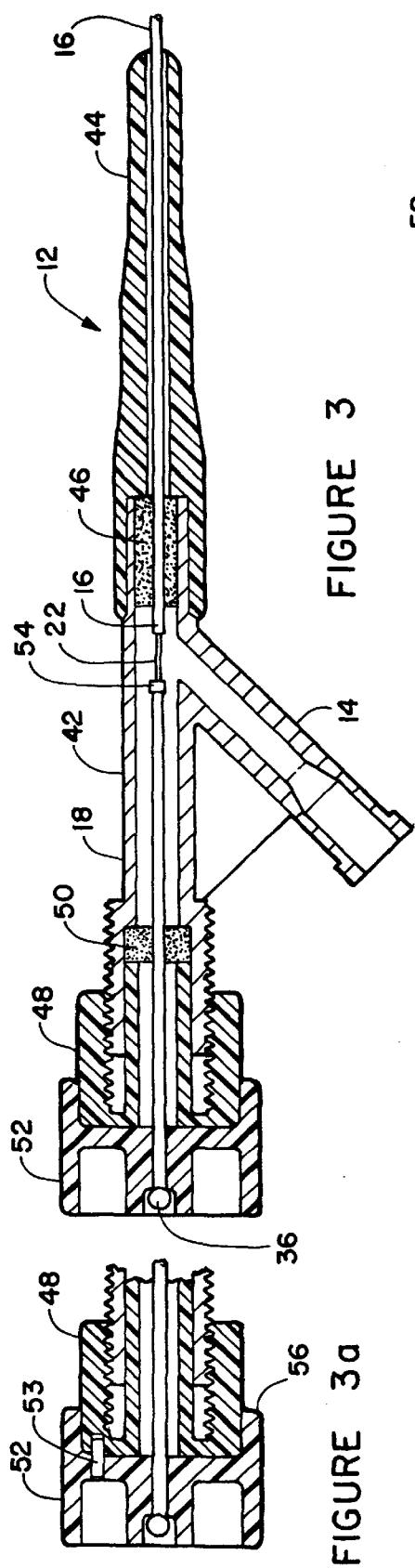
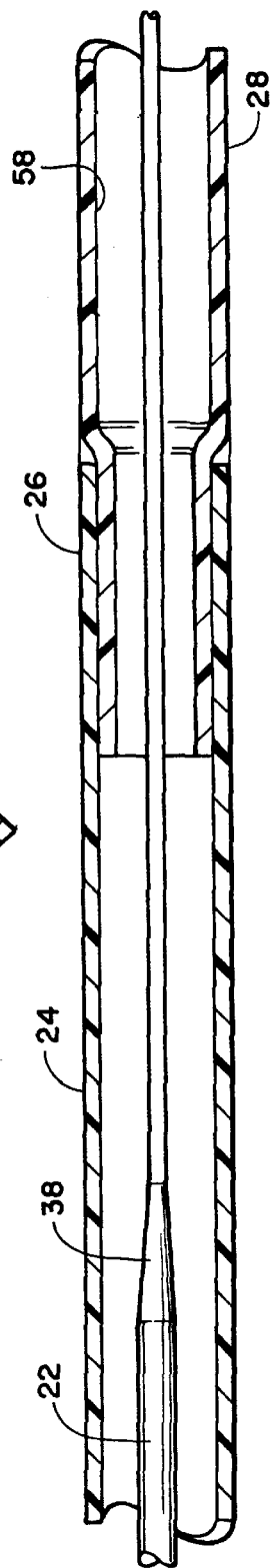
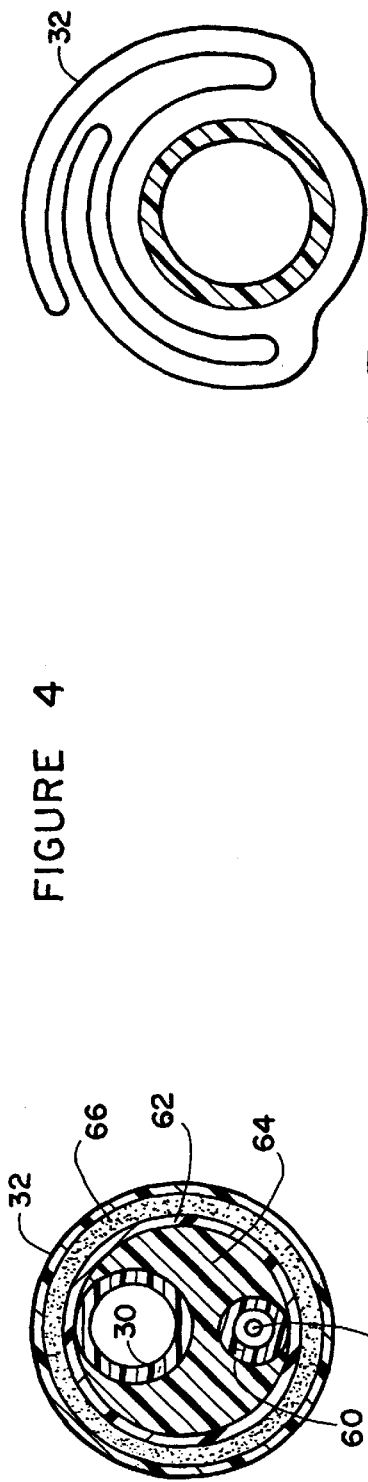

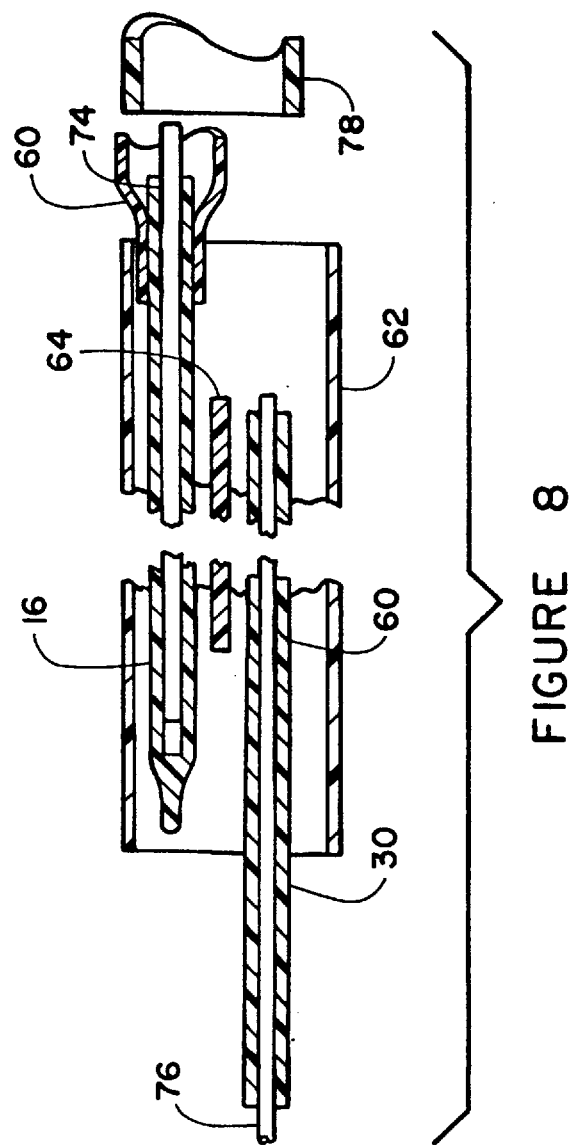

DILATATION CATHETER WITH VARIED STIFFNESS

FIELD OF THE INVENTION

This invention relates to balloon dilation catheters and, more specifically, to dual lumen adjustable stiffness exchange catheters.

Background of the Invention

Catheters comprise tube-like members inserted into body cavities for diagnostic or therapeutic medical reasons. One of the therapeutic procedures applicable to the present invention is known as percutaneous transluminal coronary angioplasty (PTCA). The first PTCA procedure was developed in approximately 1976 by Dr. Andreas Gruntzig. His fixed wire system features a core or guidewire fixed within a catheter having an inflatable balloon at the distal catheter end with the guidewire stiffening the catheter so that it could be pushed into a desired position in the vascular system. The balloon could be positioned across a blockage and inflated to cause the blockage to be decreased.

If a catheter must be exchanged for a different catheter or one of a different size, a system in which the catheter is inserted over a guidewire is advantageous because the guidewire can be left in place during catheter exchange. The catheter is withdrawn along the guidewire and another catheter is slid into place over the guide wire. Removing the catheter requires removal of the guidewire with possible problems in the guidewire recrossing the stenosis.

Alternatively, a very long "exchange" guidewire, typically about 300 cm long, may be used. Such a long guidewire is difficult and time consuming to handle, requiring two operators and the attendant risk of contamination of the guidewire through contact with objects outside the sterile field. A two-part guidewire may be used instead of the very long guidewire. This arrangement is, however, undesirable because of the additional time required for assembly and the increased thickness that may make smooth exchanges difficult.

Rapid exchange catheters have been developed to eliminate the disadvantages of the long "exchange" wire in over-the-wire systems. These catheters have short guidewire lumens passing through the balloon so that the guidewire exits from the catheter closer to the balloon than to the proximal end of the catheter. This permits the physician to hold the guidewire as he or she removes the catheter with the exchange occurring over the shorter guidewire lumen.

Typical of such rapid exchange catheters are those described by Samson et al. in U.S. Pat. No. 4,597,755, by Horzewski et al. in U.S. Pat. No. 4,748,982 and Bonzel in U.S. Pat. Nos. 4,762,129 and 5,232,445. Short guidewire lumens through or along side the balloon are described by Kontos et al. in U.S. Pat. No. 5,180,367. Arrangements for varying the stiffness of catheters in over-the-wire catheters to aid in controlled insertion have been described by Hess in U.S. Pat. No. 4,927,413 and Scopton et al. in WO Patent No. 92/17236. An adjustable stiffness dilation catheter is described by Fugoso et al in U.S. Pat. No. 5,545,138.

While many of these arrangements provide acceptable results when used by a skilled practitioner, problems remain. Many of the multi-lumen catheters, especially those with two lumens, one for movement along a guide wire and the other for balloon inflation liquid and for a variable stiffening wire have an oval or elliptical cross section with a maximum diameter greater than is desirable. Further, the degree of stiffness along different portions of the catheter is not optimum and cannot be varied to the degree desired. Where the distance over which a stiffening wire can be inserted into a catheter is variable, maintaining a particular desired insertion distance is often difficult. Thus, there is a continuing need for improved dilation catheters in which stiffness along the length of the catheter can be varied in a desired and accurately reproducible manner.

SUMMARY OF THE INVENTION

The above-noted problems, and others, are overcome in accordance with this invention by an elongated dilation catheter having a dual lumen distal end including a relatively short first shaft for carrying a balloon and for having a first lumen for receiving and moving along a guide wire and a second, elongated, shaft having a second lumen in fluid connection with the balloon and for simultaneously receiving a stiffening wire for movement between predetermined positions within said second lumen. The proximal end of said second lumen is operatively connected to a manifold for introducing fluid into said second lumen and for moving the stiffening wire along said second lumen.

The first and second shafts and corresponding lumens are secured together in parallel. The catheter has a generally circular cross section in this region, provided by a novel forming process.

For optimum effectiveness, the stiffening wire tapers in a stepped manner from a maximum diameter at the proximal end, stepping down to a narrower diameter at a selected catheter mid-point and stepping to a still narrower diameter near the balloon proximal end.

A handle means is secured to the proximal end of the stiffening wire at the catheter proximal end for varying the insertion of the stiffening wire into said second lumen over a predetermined movement distance. A positive stop is provided to assure consistent, reproducible, maximum insertion of the stiffening wire into said second lumen. Further, a positive stop is also preferably provided at the catheter distal end to consistently limit the maximum insertion of the stiffening wire relative to the balloon. The positive stop prevents damage to the balloon interior and provides for transmission of force thereto.

It is an object of this invention to provide a stiffening wire having improved adjustability and optimum stiffness variation along the catheter length for enhanced pushability and trackability. Another object is to provide positive, reproducible, stops to assure the optimum maximum stiffening wire insertion and tip location relative to the balloon. A further object is to provide a dual lumen catheter having a substantially round external cross section.

BRIEF DESCRIPTION OF THE DRAWINGS

Details of the invention, and of preferred embodiments thereof, will be further understood upon reference to the drawing, wherein:

FIG. 1 is a plan view of the catheter assembly of this invention;

FIG. 2 is a plan view of the stepped stiffening wire;

FIG. 3 is a section view through the manifold assembly shaft region;

FIG. 3a is a detail axial section view through an alternative embodiment of the handle portion of the manifold assembly;

FIG. 4 is a generally axial section view through the proximal to mid-joint shaft section;

FIG. 6 is a transverse section view taken on line 6—6 in FIG. 5;

FIG. 7 is a transverse section view taken on line 7—7 in FIG. 5 with the balloon in the wrapped configuration;

FIG. 8 is the manufacturing assembly; and

DETAILED DESCRIPTION OF PREFERRED EMBODIMENTS

Figure 5:
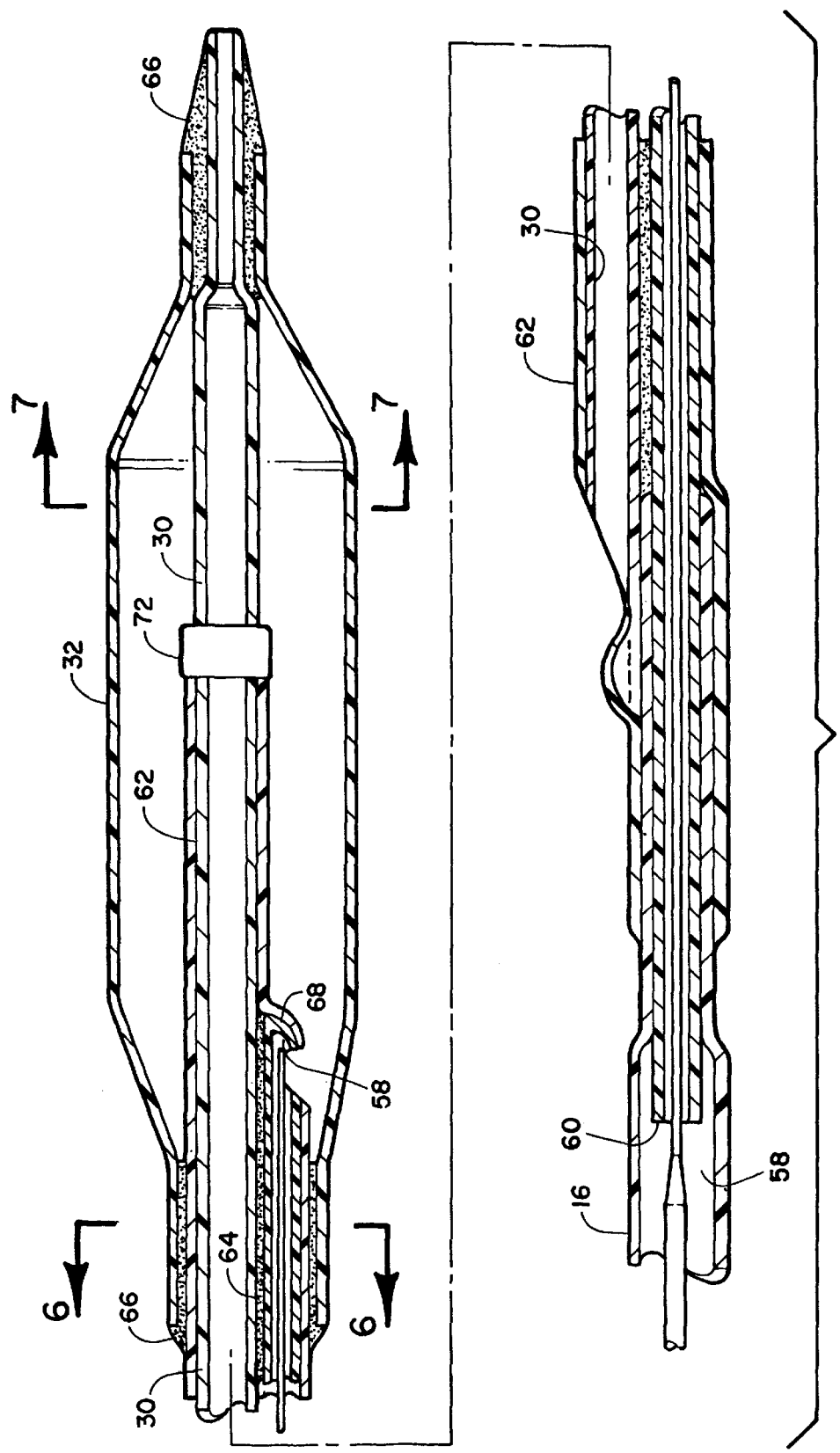
FIG. 5 is a generally axial section view through the balloon assembly and rail section.

Referring to FIG. 1, there is seen a dilation catheter 10 having adjustable stiffness and the other features of this invention. Basically, catheter 10 includes a manifold 12 (detailed in FIG. 3) having a first branch 14 for the introduction of pressurized liquid into a longitudinal balloon inflation lumen running the length of balloon inflation shaft 16. Manifold 12 includes a second branch 18 through which a stiffening wire 22, as seen in FIG. 2, is inserted into the balloon inflation lumen. A handle 20 on branch 12 is secured to the proximal end of the stiffening wire 22 and adjusts the distance the wire is inserted into a catheter lumen, as detailed below. Balloon inflation shaft 16 preferably is formed from two or more materials in two or more sections. In the embodiment shown, a proximal section 24 is made from a relatively stiff material for optimum pushability connected at joint 26 (as detailed in FIG. 4) to a relatively more flexible material for optimum trackability. The midshaft section is connected to a more stiff distal section as detailed in FIG. 5 for improved lesion crossing. As seen in FIG. 1, section 24 is connected at joint 29 to a stiffer distal section 28 for lesion crossing.

A guidewire shaft 30, (as detailed in FIG. 5) is provided at the distal end of distal section 28, secured to balloon inflation shaft 16 adjacent to and extending through balloon 32 (as shown in cross section in FIG. 5). Guidewire shaft 30 is substantially parallel to balloon inflation shaft 16 and is surrounded by a filler material and tube assembly as detailed in FIG. 6.

A typical stiffening wire 22 for insertion into the balloon inflation lumen of a balloon catheter is shown in FIG. 2. Wire 22 has a length such that when fully inserted into the balloon inflation lumen within balloon inflation shaft 16 the distal wire end will lie at a predetermined location adjacent to balloon 32. The proximal end 36 of stiffening wire 22 includes means for connection to handle 20. An enlarged ball-like end may be provided for snapping into a corresponding aperture in handle 20. Alternately, a hook like end or other shape, mechanically or adhesively secured to handle 20 may be used if desired.

Stiffening wire 22 is reduced in diameter in steps from the proximal to the distal end to provide maximum stiffness and pushability at the proximal end and lower stiffness and greater trackability near the distal end. Wire 22 also is dimensioned to provide adequate inflation and deflation times. While stiffening wire 22 can be formed from any suitable material, stainless steel or nitinol are preferred for an optimum combination of stiffness and formability. For optimum performance, the distal end of stiffening wire 22 has a diameter of from about 0.004 to 0.008 in. and extends to a location about 1 to 10 mm into the balloon 32. The proximal section of wire 22 is stepped to a diameter of from about 0.006 to 0.011 inch from about 0.004 to 0.008 inch at first step 38. The mid-section extends to second step 40. At second step 40, wire 22 is preferably stepped down to a diameter of from about 0.004 to 0.008 inch. The distal end of stiffening wire 22 preferably extends to a position inside balloon 32 when fully inserted.

Details of manifold 12 are shown in an axial section view in FIG. 3. Manifold body 42 includes a first branch 14 through which pressurized fluid medium can be introduced into the balloon inflation lumen within balloon inflation shaft 16. A second branch 18 permits straight-line entry of stiffening wire 22 into the balloon inflation lumen. A flexible nose piece 44 (for strain relief) is secured to the distal end of manifold body 18 and surrounds the proximal end of balloon inflation shaft 16. A sealant 46, typically an adhesive such as cyanoacrylate or epoxy resin that is curable by visible or ultraviolet light, secures the distal end of balloon inflation shaft 16 to manifold body 18.

A cap 48 is threaded into the open proximal end of second manifold branch 18. An elastic seal 50, typically a silicone or urethane resin ring, is interposed between cap 48 and body 18. Stiffening wire 22 enters through an axial opening in seal 50 and passes into the balloon inflation lumen in balloon inflation shaft 16. The proximal end of stiffening wire 22 is secured to a handle 52 that abuts cap 48. Cap 48 can be tightened to compress seal 50 to prevent pressurized fluid leakage (positive or negative) along wire 22 through the cap while still allowing movement of the stiffener.

A stop ring 54 is preferably formed around stiffening wire 22 at a predetermined distance from seal 50. A hypotube support cover may be used in which stiffening wire 22 is placed to provide support when the handle is separated from the manifold at cap 48. The distance the stiffening wire is inserted into the balloon inflation lumen can be varied by moving handle 52 relative to cap 48. Maximum insertion occurs when handle 52 is in abutting contact with the end of cap 48. Minimum insertion occurs when handle 52 is moved away from cap 48 to the point where stop ring 54 engages seal 50.

Handle 52 includes a tubular flange 56 that is a tight friction fit over cap 48. This will prevent accidental movement of handle 52 away from cap 48 during use of the catheter.

If desired, a keying arrangement between cap 48 and handle 52, such as a pin-like projection 53 (As seen in FIG. 3a) on the inner surface of handle projecting into a corresponding recess in cap 48, a pattern of interlocking ridges and grooves between handle 52 and cap 48, etc., so that rotation of handle 52 with the interlock engaged through contact between cap and handle will rotate cap 48 between a tight and loose seal configuration.

In general, it is desirable for the proximal portion of balloon inflation shaft 16 to have greater stiffness for optimum pushability when inserting the catheter into a body vessel and for the distal portion to have greater flexibility for improved tracking along curved vessels. To aid in this stiffness variation, a transition region is provided as shown in axial section view in FIG. 4. Proximal section 24 of the balloon inflation shaft 16 is preferably formed from a relatively stiff material, such as a polyimide. Distal section 28 is preferably formed from a more flexible, low distortion, material, such as polyethylene. Any other suitable materials having these desired characteristics may be used. The two materials are joined together at an overlapping, adhesively bonded joint 26.

In order to further and variably adjust the stiffness of the catheter, the stepped stiffening wire 22 is positioned in the inflation lumen 16. The first stepped decrease in thickness preferably is positioned in the general area of joint 26. As described above, by moving handle 52 the specific position of step 38 can be varied relative to joint 26.

Details of balloon 32, guidewire shaft 30 and related components are shown in the axial section view of FIG. 5 and the transverse section views of FIGS. 6 and 7.

Balloon 32 is shown in the inflated condition in FIG. 5 and in the folded condition in FIG. 7. A pressure resistant material, such as polyethylene or Nylon, that can be heat set to form the folds of FIG. 7, then expand into the round inflated shape is preferred.

The distal end of balloon inflation shaft 16 is shrunk around, and bonded to an extension of the balloon inflation shaft 60 which extends to a point just within balloon 32. Guidewire shaft 30 lies parallel and adjacent to inflation shaft 16. Reinforcing tubing 62 surrounds both inflation shaft 60 and guidewire shaft 30, with a filler 64 (introduced as detailed below) filling the space between tube 62 and the shafts. Reinforcing tube 62 is preferably formed from a high strength heat shrink tubing that naturally forms a circular cross section when shrunk while pressurized, such as polyethylene. The proximal end of balloon 32 is bonded to the exterior of reinforcing tubing 62 by a layer 66 of adhesive, such as a visible light or ultraviolet light curable epoxy, cyanoacrylate or a heat shrink bond. The distal end of balloon 32 is also bonded to guidewire shaft 30 by a layer of adhesive 66 or a heat shrink bond.

The distal end 68 of inner shaft 60 is closed by melting, with the reinforcing tubing 62 thereover. A skived out notch is cut through the reinforcing tubing 62 and inflation shaft 60 adjacent to distal end 68 to provide for fluid communication between the balloon inflation lumen 58 and the interior of balloon 32.

The distal end of stiffening wire 22 extends through the extended balloon inflation lumen within inner shaft 60. When fully inserted, stiffening wire 22 encounters the closed end of tubes 60 and 62 at 68, which provides a positive stop for full insertion, enables force transmission and prevents inadvertent excessive insertion and/or damage to the interior of balloon 32.

The distal end of stiffening wire 22 can be withdrawn any desired distance, corresponding to the distance between stop ring 54 when handle 52 abuts cap 48 and stop ring 54 when withdrawn into contact with seal 50, as seen in FIG. 3.

Preferably, marker bands 72 are provided at suitable locations within balloon 32 and at predetermined locations along balloon inflation shaft 16. Marker bands 72 are formed from any suitable radio opaque material so that their positions can be clearly seen by X-ray fluoroscopy during catheter insertion. Typical such materials include gold, iridium, platinum and mixtures or alloys thereof.

As mentioned above, in the past when a guidewire shaft and a balloon inflation shaft were bonded together to provide a short guide wire shaft alongside the balloon inflation shaft, the assembly had an oval or elliptical cross section. This shape resulted in problems in inserting the catheter and in bonding such an elliptical assembly cross section to the optimally circular balloon.

Figure 9:
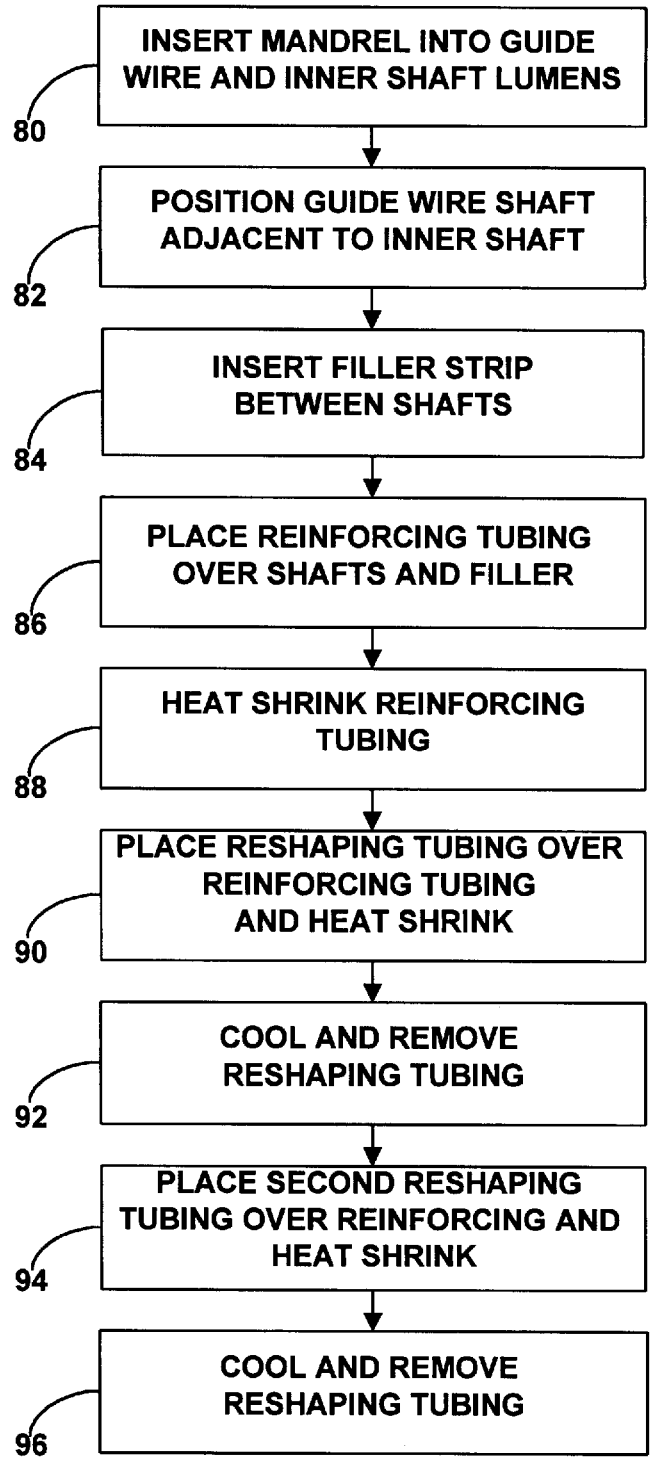
FIG. 9 is the method of manufacturing block diagram.

An ideal generally circular cross section, as seen in FIG. 6, can be produced by the method schematically illustrated in FIG. 8 and in the block diagram of FIG. 9.

Initially, as seen in FIG. 8 and per block 80 of the flow diagram of FIG. 9, release-coated wire mandrels 74 and 76 (typically Parylene coated stainless steel wires) are inserted into the tube that will become the guidewire shaft 30 and into a mid-distal tube assembly that will become the distal end of balloon inflation shaft 16 and the inner shaft, respectively. Guide wire shaft 30 and the mid/distal assembly are then positioned in the desired overlapping relationship, block 82.

A suitable filler material strip 64 is then inserted between the two shafts, block 84. Any suitable filler material, such as polyethylene, that will melt at a temperature below a temperature at which any of the other components would degrade may be used. While filler strip 64 may have any suitable configuration, a strip cut lengthwise from a piece of tubing, typically about a quarter-round cut from a 0.023 in. outside diameter, 0.0035 in. wall thickness tube, having a crescent-like cross section, is preferred for ease of assembly.

Reinforcing tubing 62 is then slipped over the resulting assembly (guidewire shaft 30 and balloon inflation shaft 60), block 86. Tubing 62 should be a heat shrink material that will shrink at a temperature just above the melting temperature of filler strip 64. Typically, reinforcing tube 62 may be formed from polyethylene or nylon As tubing 62 shrinks, block 88, the assembly takes on a generally oval cross section.

A reshaping tube 78 (as seen in FIG. 8) of a stiff material that naturally assumes a circular cross section is forced over the assembly, (guidewire shaft 30 and balloon inflation shaft 60), and heat shrunk, (see block 90) sufficiently tight to force the assembly into a round configuration. For the purposes of this application, "stiff" means having sufficient stiffness to return to, or remain in, a substantially circular cross section when filled with a molten liquid at just above its melting temperature. While any suitable material may be used for reshaping tube 78, tetrafluroethylene is preferred because of its heat shrinkability, low friction and non-bondable characteristics. In some cases, this tube will produce a sufficiently round shape to the assembly. In that case, the assembly is cooled, block 92, and reshaping tube 78 is removed. In order to produce a more precisely circular cross section in the assembly, after partial cooling, the original reshaping tube 78 can be removed and a smaller diameter reshaping tube can be emplaced, block 94. The smaller diameter reshaping tube is then heat shrunk, cooled and removed, block 96. The resulting substantially round assembly is more easily passed along a body vessel and when bonded to a balloon produces a more uniformly round inflated balloon.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A dilation catheter comprising:
   a balloon inflation shaft defining a balloon inflation lumen and having a distal end and a proximal end;
   a balloon affixed to the balloon inflation shaft distal end and in fluid communication with said balloon inflation lumen;
   a stiffening wire having a distal end and a proximal end extending through said balloon inflation lumen from said balloon inflation shaft distal end to a predetermined location near said balloon inflation shaft proximal end;
   said stiffening wire being reduced in diameter from said proximal end to said distal end in at least two steps;
   a first diameter reduction step being located at a first predetermined location spaced from said proximal end; and
   a second diameter reduction step being located at a second predetermined location spaced from said proximal end a greater distance than said first diameter reduction step;

whereby said balloon inflation shaft and stiffening wire produces improved pushability near the balloon inflation shaft proximal end and improved trackability near the balloon inflation shaft distal end; and wherein said stiffening wire has a means for advancing and retracting said stiffening wire within said balloon inflation shaft.

2. The dilation catheter according to claim 1 wherein said stiffening wire is reduced in diameter from about 0.012 to 0.016 inch to about 0.010 to 0.008 inch at said first step and to from about 0.004 to 0.008 inch at said second step.

3. The dilation catheter according to claim 1 wherein said proximal end of said balloon inflation shaft has a first predetermined stiffness and said distal end of said balloon inflation shaft has a second predetermined stiffness less than said first predetermined stiffness, said proximal and distal ends being connected together at a predetermined connection location, and said first reduction in stiffening wire diameter is located approximately at said connection location.

4. The dilation catheter according to claim 1 further including means along said balloon inflation lumen adjacent to said balloon for limiting the distance said stiffening wire can be inserted into said balloon inflation lumen.

5. The dilation catheter according to claim 1 further including positive stop means adjacent to the balloon proximal end for preventing further insertion of said stiffening wire and enable force transmission.

6. The dilation catheter according to claim 1 where the distal end of said stiffening wire is positioned approximately adjacent to the proximal end of said balloon.

7. The dilation catheter according to claim 1 further including means adjacent to said balloon inflation lumen proximal end for moving said stiffening wire between a first advanced position and a second retracted position within said balloon inflation lumen over a predetermined range.

8. A dilation catheter comprising:

a balloon inflation shaft defining a balloon inflation lumen and having a distal end and a proximal end;

a balloon affixed to the balloon inflation shaft distal end and in fluid communication with said balloon inflation lumen;

a stiffening wire having a distal end and a proximal end extending through said balloon inflation lumen from said balloon inflation shaft distal end to a predetermined location near said balloon inflation shaft proximal end;

a manifold connected to said balloon inflation shaft proximal end for directing fluid and said stiffening wire into said balloon inflation lumen;

said manifold having a substantially straight longitudinal channel therethrough having a distal channel end receiving the proximal end of said balloon inflation shaft and bonded thereto and having a proximal channel end through which said stiffening wire proximal end extends;

a seal surrounding said stiffening wire adjacent to said proximal channel end for preventing fluid egress while permitting said stiffening wire proximal end to be moved between a first advanced position and a second retracted position relative to said proximal channel end within a predetermined range;

a cap over said proximal channel end for increasing and decreasing pressure of said seal against said wire;

a handle over said cap means secured to the proximal end of said stiffening wire for moving said stiffening wire over said predetermined range;

a stop on said stiffening wire within said manifold for limiting movement of said handle away from said cap; and said handle including a tubular flange sized to fit over said cap in tight friction engagement therewith;

whereby said movement of said stiffening wire over said predetermined range is limited in one direction by said stop means and in the opposite direction by said handle engagement with said cap and inadvertent movement of said handle away from said cap is restricted.

9. The dilation catheter according to claim 8 further including key means between said cap and said handle.

10. A dilation catheter according to claim 1 comprising:

a guidewire shaft defining a guidewire lumen extending through said balloon parallel and adjacent to said balloon inflation shaft;

a substantially circular tube having an interior volume surrounding said guidewire shaft and at least a predetermined portion of said balloon inflation shaft; and filler material filling said interior volume around said guidewire shaft and balloon inflation shaft;

whereby said circular tube is maintained in a substantially circular state.

11. The dilation catheter according to claim 10 wherein said substantially circular tube is formed from low density polyethylene and said filler material is a low density polyethylene.

* * * * *